(12) United States Patent
Gutnick et al.

(10) Patent No.: US 6,512,014 B2
(45) Date of Patent: Jan. 28, 2003

(54) COMPOSITIONS CONTAINING BIOEMULSIFIERS AND A METHOD FOR THEIR PREPARATION

(75) Inventors: David Gutnick, Sharon Hatichon (IL); Horacio R. Bach, Doar Na Misgav (IL)

(73) Assignee: Ramot University Authority for Applied Research and Industrial Development Limited, Tel Aviv (IL)

( * ) Notice: Subject to any disclaimer, the term of this patent is extended or adjusted under 35 U.S.C. 154(b) by 57 days.

(21) Appl. No.: 09/734,895

(22) Filed: Dec. 13, 2000

(65) Prior Publication Data

US 2002/0143071 A1 Oct. 3, 2002

(51) Int. Cl.7 .................................. B01F 17/00
(52) U.S. Cl. ..................... 516/70; 210/925; 435/68.1; 435/101; 435/823; 510/365; 930/240
(58) Field of Search .................. 516/70; 210/925; 510/365; 435/823, 68.1, 101; 930/240

(56) References Cited

U.S. PATENT DOCUMENTS

| 4,395,353 A | | 7/1983 | Gutnick et al. | 210/925 X |
|---|---|---|---|---|
| 4,693,842 A | | 9/1987 | Shilo et al. | 210/925 X |
| 4,793,826 A | * | 12/1988 | Hayes et al. | 516/70 X |
| 5,472,629 A | * | 12/1995 | Lysy et al. | 570/365 X |
| 5,494,580 A | * | 2/1996 | Baskys et al. | 435/823 X |
| 5,508,176 A | * | 4/1996 | Hillen et al. | 930/240 X |
| 5,840,547 A | | 11/1998 | Rosenberg et al. | 435/71.2 |
| 6,063,602 A | * | 5/2000 | Prosperi et al. | 516/70 X |

* cited by examiner

Primary Examiner—Richard D. Lovering
(74) Attorney, Agent, or Firm—Lowe Hauptman Gilman & Berner, LLP

(57) ABSTRACT

A bioemulsifier composition useful for forming and stabilizing oil-in-water emulsions, comprising an esterase protein of 32.5 KD, found in association with emulsan in the bacteria Acinetobacter. The esterase, or parts of it, are isolated from cell extracts of various strains of Acinetobacter, or produced by any other means. The bioemulsifier composition is further comprised of a water-soluble polysaccharide polymer of any source. The present invention further discloses a method of forming and stabilizing oil-in-water emulsions, using the above-mentioned composition.

13 Claims, No Drawings

COMPOSITIONS CONTAINING BIOEMULSIFIERS AND A METHOD FOR THEIR PREPARATION

FIELD OF THE INVENTION

The present invention generally relates to emulsifiers of biological origin, for use in numerous industries such as environmental management, health care, dental care, cosmetics and food product applications. The present invention further relates to a method for the production of said emulsifiers of biological origin, (herein after also called a "bioemulsifier"), using an esterase protein originating from the bacteria Acinetobacter, in combination with one of a variety of polysaccharides or biopolymers. The bioemulsifier composition thus obtained stabilizes a variety of oil-in-water emulsions. Since the bioemulsifier composition is versatile in regard to the biopolymer or polysaccharide used in the emulsification, many non-toxic polymers that are already widely in use, for example in the cosmetic or food industries, can be employed.

BACKGROUND OF THE INVENTION

Bioemulsifiers are biological products that aid in the formation and stabilization of water-in-oil or oil-in-water emulsions. Unlike classical detergents whose activity is generally to reduce interfacial tension at the interface of two immiscible liquids thereby lowering the energy required to generate emulsions, amphipathic biopolymeric bioemulsifiers generally work by orienting themselves at the oil/water interface, in such a way that they interfere with coalescence of the oil droplets. This in turn stabilizes the emulsion, reducing the tendency of the droplets to coalesce.

Emulsifiers of biological origin are preferred over synthetic emulsifiers in instances where their use may have an impact on the environment, such as containment of oil spills, since bioemulsifiers are biodegradable, and are less likely to leave toxic by-products behind. In addition, bioemulsifiers may be relatively inexpensive to produce. U.S. Pat. No. 4,693,842 (Shilo) discloses a biopolymer purified from a cyanobacterium, which is useful in flocculation. U.S. Pat. No. 5,840,547 discloses a bioemulsifier named Alasan, originating from the bacteria *Acinetobacter radioresistens* strain KA53; and a method for its production.

There is previously disclosed in U.S. Pat. No. 4,395,353 (by the current applicant), a polymeric polyanionic, aminopolysaccharide, water-soluble bioemulsifier termed emulsan (molecular mass, $10^6$) which is produced by an oil-degrading microorganism, *Acinetobacter lwoffii* RAG-1. Emulsan forms and stabilizes oil/water emulsions using a variety of hydrophobic substrates. The aminopolysaccharide backbone is composed of repeating subunits of a trimer consisting of D-galactosamine, D-galactosamine uronic acid, and bacillosamine (2, 4 diamino, 6-deoxy glucose). The amphipathic character of the biopolymer is due in large part to the presence of about 25% (w/w) acyl groups linked to the polymeric backbone in both ester, and amide linkages. The fatty acids vary in chain length from 2–18. In addition, a significant percentage of the fatty acids are hydroxylated (i.e. β-hydroxy butyrate and β-hydroxydodecanoic acid). During exponential growth the biopolymer is present on the cell-surface as a minicapsule and is released as a protein-polysaccharide complex as the cells enter stationary phase. Emulsan release is mediated by the action of a cell-surface esterase, which also constitutes one of the major proteins associated with emulsan. The non-covalently attached protein (between 15 and 25% by weight) can be removed from the polymer to generate a de-proteinated, partially active amphipathic bioemulsifier termed apoemulsan. The deproteinized apoemulsan is much less efficient in stabilizing very hydrophobic substrates. This hydrophobic activity can be partially restored by the addition of crude protein.

Emulsan technology was used as an industrial product in a host of cleaning and degreasing applications in ships, barges, storage tanks and various industrial environments. The U.S. Navy research labs have described the use of emulsan in the cleaning of sludge filters for all of their ships. In addition, emulsan was formulated for application in viscosity reduction of heavy oils and sludges by generating low viscosity homogeneous oil/water emulsions.

Emulsan is potentially toxic, since in crude form it is frequently contaminated with toxigenic lipopolysaccharide characteristic of all gram-negative organisms. Emulsan, therefore, must be highly purified in order to find uses in such applications as health care, dental care, cosmetics and food product applications.

It is the object of the present invention to provide novel amphipathic bioemulsifier compositions, which are non-toxic, versatile and relatively inexpensive to produce. Some of these compositions utilize non-toxic polymers that are already widely in use in various industries of commercial value such as the food and cosmetic industries, hence these polymers are considered both safe and inexpensive to employ. The novel compositions disclosed here allow emulsan technology to be more widely applied, since they are far more removed from the Acinetobacter bacteria than previously characterized emulsan compositions. Hence they need not contain contaminants typical of gram-negative bacteria.

It is also an object of the present invention to provide a method for producing the heresaid bioemulsifier compositions.

These and other objects of the present invention will become more apparent from the summary of the invention and the detailed description of the preferred embodiments, that follow.

SUMMARY OF THE INVENTION

The present invention relates to a bioemulsifier composition for forming and stabilizing oil-in-water and emulsions, comprising:

a) an esterase protein of 32.5 KD, wherein said protein is normally found in association with emulsan in the bacteria Acinetobacter, isolated from cell extracts from at least one strain of Acinetobacter; or recombinant preparations of said esterase protein isolated from esterase-producing vectors expressed in suitable hosts, or, peptide fragments of said esterase protein produced in any of a variety of means, including proteolysis or genetic cloning;

b) water-soluble polysaccharide polymer of any source, including bacterial, plant and synthetic sources; or biopolymers such as polyanionic heteropolysaccharides.

Further in accordance with a preferred embodiment of the present invention, the polysaccharide is selected from agarose, gum arabic, carrageenan, pectin, potato starch, xanthan, dextran, alginic acid, cellulose, chitin, colanic acid, ficoll 400, pullulan, polyvinyl pyrrolydone, stewartan, xylan or *Acinetobacter calcoaceticus* BD4 exopolysaccharide. It is appreciated, however, that any synthetic or biological polymer or polysaccharide may be employed as well.

Additionally in accordance with a preferred embodiment of the present invention, a stabilizer or a co-emulsifier can be added to the composition.

Still further in accordance with a preferred embodiment of the present invention, emulsan or apoemulsan are added to the composition, as a stabilizer or co-emulsifier.

Further in accordance with a preferred embodiment of the present invention, low molecular weight surfactants are added to the composition.

Moreover in accordance with a preferred embodiment of the present invention, the esterase protein is derived from Acinetobacter strain *A. lwoffi* RAG-1 and has the following amino acid composition:

Met lys phe gly thr val trp lys tyr tyr phe thr glu ser leu leu lys

Ala thr ile arg thr pro ser gln leu asn leu ala pro asn ala leu

Arg pro val leu asp gln leu cys arg leu phe pro gln asn pro

Thr val gln ile arg pro ile arg leu ala gly val arg gly glu glu

Ile lys ala gln ala ser ala thr gln leu ile phe his ile his gly

Gly ala phe phe leu gly ser leu asn thr his arg ala leu met

Thr asp leu ala ser arg thr gln met gln val ile his val asp tyr

Pro leu ala pro glu his pro tyr pro glu ala ile asp ala ile phe asp val

Tyr gln ala leu leu val gln gly ile lys pro lys asp ile ile ile ser gly

Asp ser cys gly ala asn leu ala leu ala leu ser leu arg leu lys gln

Gln pro glu leu met pro ser gly leu ile leu met ser pro tyr leu

Asp leu thr leu thr ser glu ser leu arg phe asn gln lys his asp

Ala leu leu ser ile glu ala leu gln ala gly ile lys his tyr leu thr

Asp asp ile gln pro gly asp pro arg val ser pro leu phe asp asp leu

Asp gly leu pro pro thr leu val gln val gly ser lys glu ile leu leu

Asp asp ser lys arg phe arg glu lys ala glu gln ala asp val lys

Val his phe lys leu tyr thr gly met trp asn asn phe gln met

Phe asn ala trp phe pro glu ala lys gln ala leu ala asp ile ala

Glu phe ala thr ser leu asp leu asp.

Additionally in accordance with a preferred embodiment of the present invention, the esterase protein is derived from the Acinetobacter strain *A. calcoaceticus* BD4.

Further in accordance with a preferred embodiment of the present invention, the esterase protein is derived from the Acinetobacter strain *A. calcoaceticus* BD13.

There is also provided in the present invention a method of forming and stabilizing an oil-in water emulsion, comprising:

a) adding esterase protein of 32.5 KD, found in association with the emulsan protein in the bacteria Acinetobacter, isolated from cell extracts from at least one strain of Acinetobacter, or recombinant preparations of said esterase protein isolated from esterase-producing vectors expressed in suitable hosts, or peptide fragments of said esterase protein produced in any of a variety of means, including proteolysis or genetic cloning;

b) adding water-soluble polysaccharide polymer of any source, including bacterial, plant and synthetic sources; or biopolymers such as polyanionic heteropolysaccharides.

Additionally in accordance with a preferred embodiment of the present invention, the method further comprises the step of adding a stabilizer or emulsifier.

In accordance with a preferred embodiment of the present invention, the method further comprises the step of adding emulsan or apoemulsan.

Moreover in accordance with a preferred embodiment of the present invention, the method further comprises the step of adding low molecular weight surfactants.

BRIEF DESCRIPTION OF THE TABLES

The present invention is herein described, by way of example only, with reference to the accompanying tables, wherein:

Table 1 illustrates emulsifying activity of various bioemulsifier compositions, which comprise esterase protein combined with different polysaccharides.

Table 2 illustrates emulsifying activity of apoemulsan together with esterase protein, acting on various hydrophobic substrates.

Table 3 illustrates emulsifying activity of apoemulsan combined with various mutants of the esterase protein or with fragments of the esterase protein.

Table 4 illustrates emulsifying activity of apoemulsan combined with various proteins of diverse origin.

DETAILED DESCRIPTION OF THE PREFERRED EMBODIMENTS

It is appreciated that the detailed description that follows is intended only to illustrate certain preferred embodiments of the present invention. It is in no way intended to limit the scope of the invention, as set out in the claims.

The present invention relates to the ability of an enzyme, the cell-surface esterase of the emulsan-producing bacterium Acinetobacter species RAG-1 to interact with a series of biopolymers and bacterial polysaccharides in order to generate an amphipathic bioemulsifer composition. We had previously shown that this exocellular enzyme was involved in the release of emulsan into the growth medium during the fermentation of the biopolymer. The enzyme is one of a series of proteins which appears in the broth along with the biopolymer. We have isolated the gene encoding this enzyme, determined its sequence and overexpressed it in *E. coli* so that it can constitute 5–30% of the total cellular protein. The enzyme can be added to a fresh preparation of deproteinized apoemulsan. The resulting mixture has been shown to bring about the emulsification of a host of very hydrophobic compounds such as aliphatic alkanes (from C12–C18) which are normally not emulsified by emulsan. Additional substrates include phenanthrenes, naphthalenes and other polycyclic aromatic hydrocarbons (PAH's) and several sludges and insoluble aggregates which were taken from various storage tank bottoms.

Surprisingly and unexpectedly, both wild-type and mutant recombinant esterases were found to interact with the capsular exopolysaccharide of a second Acinetobacter species, *A. calcoaceticus* BD413. The resulting esterase-polysaccharide mixture was found to constitute a potent bioemulsifying complex.

Referring to Table 1, the esterase preparations were tested with a variety of biopolymer preparations including starch, cellulose, chitin, pullulan, pectin, colanic acid, stewartan, alginate, and xanthan. In all cases the resulting protein-biopolymer complex was found to bring about the emulsification of a variety of hydrocarbon substrates; esterase converts biopolymers to amphipathic emulsifiers. Table 1 shows the unexpected stimulation of emulsifying activity brought about by mixing any of 20 different polysaccharides with the recombinant esterase at a ratio of one part esterase to ten parts of biopolymer and 700 parts of hexadecane in 10 ml. water. The mixtures were shaken for an hour at 30 C. on a reciprocal shaker at 150 strokes per minute, and the turbidities assayed using either a spectrophotometer or a Klett Summerson Colorimeter. One unit of emulsifying activity gives rise to an emulsion turbidity of 100 KU. The specific emulsifying activity presented in Table 1 is expressed as U/mg biopolymer/mg esterase (UpBPE). The results are expressed as net emulsifying units and are corrected for emulsification in the absence of the protein. The control activity was never greater than 0.25 units of emulsifying activity. As expected, none of the biopolymers exhibited any appreciable activity in the absence of the esterase protein. Activities varied between 6–7,500 UpBPE (U/mg polymer/mg esterase) for emulsan and apoemulsan, respectively to about 260 UpBPE for the synthetic polymer Ficoll 400. Usual activities were in the range of 1000–2000 UpBPE. Polysaccharides from a variety of bacterial, plant and synthetic sources were all active to some extent. Moreover, many of the polymers such as gum arabic, cellulose, pectin, starch, xanthan, etc. are already commercial products in areas such as the food industry and could be incorporated as emulsifiers for approved use.

Table 1 also illustrates the stabilities of some of the hexadecane/water emulsions stabilized by the biopolymer-esterase compositions. The stabilities are estimated by the percent-decrease in turbidity following a period in which the emulsions were allowed to stand for an hour and the turbidity monitored after 60 minutes without agitation. Shown in this table are examples of stabilities of emulsions formed with recombinant esterase mixed with emulsan, apoemulsan, carrageenan, pectin, gum Arabic and the extracellular polysaccharide from the strain *Acinetobacter calcoaceticus* BD4. While the emulsifiers showed varying levels of emulsification, most of the emulsions generated by the compositions showed a decrease in turbidity of less than 20% of the original after standing for an hour, demonstrating that that the esterase compositions were effective as emulsion stabilizers regardless of the biopolymer. Thus, emulsion stabilization may prove to be a useful application within the food, health care and cosmetics industries.

The emulsan biopolymer and its deproteinated derivative, apoemulsan, are not particularly active as emulsifiers using very hydrophobic hydrocarbon substrates such as hexadecane. In order to obtain strong emulsification it is generally necessary for the hydrocarbon substrate to consist of a mixture of aliphatic and aromatic hydrocarbons.

Referring to Table 2, a variety of crude and refined petroleum products including very hydrophobic refinery sludge (of unknown age and composition) can be emulsified using the esterase-apoemulsan composition. Moreover, even insoluble hydrocarbons such as anthracene were emulsified. Results in Table 2 demonstrate that the range of oils emulsified by the apoemulsan and/or emulsan polymers can be dramatically extended using the esterase-polysaccharide composition. Moreover, the hydrophobic substrates are not restricted to petroleum products. Using these compositions, a number of other vegetable and mineral oils were also efficiently emulsified.

In addition, when the emulsifier preparations were added to preformed oil/water emulsions generated by sonic oscillation, they stabilized the emulsions, raising the half life from a few minutes, to several days. As with the emulsan biopolymer, the preformed emulsions stabilized by the complex did not separate into discrete phases, but rather generated a cream, which was readily dispersible in fresh aqueous suspensions. These preparations exhibited some other useful properties, which include:

1. The ability of the emulsifier complex to bind and concentrate heavy metals at an oil/water interface. This suggests that the emulsifier complexes can be employed in the bioremediation of heavy metals;
2. The ability of the emulsifier complexes both to remove adherent organisms from hydrophobic surfaces, and to block their re-adhesion.

The present invention comprises the emulsifier compositions using a series of either recombinant or native esterase proteins in combination with any of a large number of biopolymers. Many of the polymers are non-toxic and can therefore be applied immediately to specific applications in a variety of industrial and environmental settings. The compositions may be used in combination with low molecular weight surfactants that lower interfacial tension. Moreover, in some cases the polymers can be prepared from inexpensive commercially available products, thereby obviating the requirements for complex fermentation protocols. The invention is novel and unexpected since it involves a specific interaction of an enzyme protein which does not necessarily involve its catalytic activity but an alternative domain(s) (see Table 3, fragment 1). The ability of this enzyme to interact with a host of biopolymers that are not substrates of the enzyme, and generate an amphipathic mixture was totally unexpected.

The compositions are produced either as genetically engineered products or using classical composition technology. The invention comprises the combination of components of the compositions, which are either natural biopolymers in combination with specific recombinant or natural proteins, or peptides of specific sequence and composition, as well as technology for enhancing their production by specifically engineered microbial strains. Moreover, the active protein component or sub-fraction thereof need not be "free" peptides, rather they can be fixed to larger inactive proteins, such as the maltose-binding protein.

The composition can be prepared using native extracellular esterase protein preparations isolated from cell extracts of at least two strains of Acinetobacter, *A. lwoffii* RAG-1 or *A. calcoaceticus* BD4 or BD413. Alternatively, recombinant preparations of the enzyme isolated from esterase-producing clones over-expressed in *E. coli* can be used as well. Moreover, the enzyme need not be catalytically active in order to function. In fact, various peptide fragments of the enzyme produced either by limited proteolysis or by cloning, can replace the intact enzyme. All of the protein-biopolymer compositions showed emulsion stabilities comparable to the emulsan-stabilized emulsions. These new and novel compositions expand the uses for polymeric biosurfactants and offer new opportunities for applications using a host of non-toxic biopolymers for various applications such as cosmetics, foods, health care emulsions, as well as applications in the oil, petrochemical, agricultural and other industries as well. Applications in the petroleum industry include emulsification of various crude and refined oils as well as oily sludge wastes, clean-up, viscosity reduction, oil reclamation, heavy metal remediation, etc.

The esterase enzyme employed for the experiments described in Tables 1 and 2 were experiments using either active recombinant esterase or a partially purified enzyme from the oil-degrading emulsan producer, *A. lwoffii* RAG-1.

Referring to Table 3, a series of mutant enzymes was generated using site-directed mutagenesis. Following over-expression and purification, the mutant enzymes were tested for their ability to restore emulsification of hexadecane by apoemulsan. Thus, histidine in position 79 was converted either to alanine ($H^{79}A$) or to glycine ($H^{79}G$), while similarly, serine 149, aspartate 196, glutamate 244, histidine 274 were also converted either to alanine or to glycine respectively. Aspartate 110 was converted to glycine. In all cases the mutant enzymes were found to give rise to the emulsification of hexadecane despite the fact that none of the mutants except $D^{110}G$ showed any appreciable catalytic activity ($D^{110}G$ showed 15% catalytic activity compared to wild-type esterase). Catalytic activity is not required either for enhancement of emulsification or for emulsion stabilization. It should be noted that two of the mutants, $D^{196}G$ and $E^{244}G$ showed significantly higher emulsifying activities than any of the others, including the wild-type activities.

In addition, proteolytic digestion using chymotrypsin yielded a peptide consisting of the terminal third of the enzyme, which was as active as the intact recombinant enzyme in stimulating emulsion formation and stabilization. Thus, only a small portion of the enzyme was required for restoring emulsification activity. Peptides lacking the terminal 15 amino acids were not able to reconstitute the emulsification suggesting that the active protein fragment requires a specific amino acid composition with an appropriate C-terminus.

Referring to Table 4, several other proteins, including pancreatic lipase, bovine serum albumin and lyzozyme induced only low levels of emulsification of hexadecane. These proteins gave no enhancement above the values of apoemulsan alone. In sharp contrast, proteins such as dockerin (a protein associated with the cellulosome complex), iso-penicillin synthetase and pig esterase actually brought about a dramatic inhibition of the emulsification. These results not only demonstrate that not all proteins are effective in the emulsan enhancement compositions, but several actually serve to prevent the formation of oil/water emulsions. These proteins presumably interact with the biopolymers to prevent formation of the appropriate conformation required for enhancement of emulsification. The results support the conclusion that the observation is not based on a general interaction of proteins with emulsan polymers and other polysaccharides, but rather describes a new and non-obvious characteristic of esterase proteins normally present in at least two strains of Acinetobacter.

TABLE 1

Esterase converts biopolymers to ampipathic emulsifiers. Emulsions of hexadecane in water are formed, using one of a variety of polysaccharides in combination with recombinant esterase. Most emulsions are relatively stable.

| Polysaccharide | Maximum emulsifying activity [U/mg. polysaccharide/ mg. esterase] | Stability (Percent) |
|---|---|---|
| Emulsan | 6752 | 91 |
| Apoemulsan | 5430 | 83 |
| Agarose | 963 | |
| Alginic acid | 496 | |
| Gum Arabic | 1895 | 75 |
| BD-4 exopolysaccharide | 3396 | 88 |
| Carrageenan | 3345 | 91 |
| Cellobiose | 626 | |
| Cellulose | 766 | |
| Chitin | 540 | |
| Colanic acid | 2050 | |
| Dextran | 583 | |
| Ficoll 400 | 263 | |
| Pectin | 1830 | 81 |
| Potato starch | 544 | |
| Pullulan | 3400 | |
| Polyvinyl Pyrrolydone | 1950 | |
| Stewartan | 1196 | |

TABLE 1-continued

Esterase converts biopolymers to ampipathic emulsifiers. Emulsions of hexadecane in water are formed, using one of a variety of polysaccharides in combination with recombinant esterase. Most emulsions are relatively stable.

| Polysaccharide | Maximum emulsifying activity [U/mg. polysaccharide/ mg. esterase] | Stability (Percent) |
|---|---|---|
| Xanthan | 2720 | 79 |
| Xylan | 1854 | |

TABLE 2

Enhancement of the emulsifying activity of apoemulsan in presence of different hydrophobic substrates

| Hydrophobic substrate | Maximum emulsifying activity [U/mg. apoemulsan/mg. esterase] |
|---|---|
| Oil substrates | |
| Crude oil | 4930 |
| Diesel oil | 5200 |
| Immersion oil | 780 |
| Mineral oil | 3000 |
| Soya oil | 1260 |
| Hydrocarbon substrate | |
| Anthracene | 966 |
| Dicyclohexane | 2760 |
| Eicosane | 1800 |
| Fluoranthene | 593 |
| Heptadecane | 3417 |
| 2-Methyl Naphthalene | 1984 |
| Octadecane | 2250 |
| Petroleum refinery sludge | 1196 |
| Pyrene | 420 |
| Squalene | 600 |
| Tetracosane | 506 |

TABLE 3

Enhancement of the emulsifying activity of apoemulsan in presence of hexadecane using mutant esterases and peptide fragments.

| Esterase derivatives | Maximum emulsifying activity [U/mg. apoemulsan/mg. esterase] |
|---|---|
| Mutant esterases | |
| $H^{79}A$ | 2860 |
| $S^{149}A$ | 3200 |
| $D^{196}A$ | 1500 |
| $E^{244}A$ | 3125 |
| $H^{274}A$ | 2850 |
| $H^{79}G$ | 2675 |
| $D^{110}G$ | 1140 |
| $S^{149}G$ | 1813 |
| $D^{196}G$ | 5100 |
| $E^{244}G$ | 4800 |
| $H^{274}G$ | 2133 |
| Cloned esterase fragment 1[a] | 5890 |
| Cloned esterase fragment 2[b] | 312 |
| Chymotrypsin digest[3] | 6144 |

[1]Fragment 1 consists of the esterase lacking the N-terminal 100 amino acids.
[2]Fragment 2 is fragment 1 lacking the last 15 amino acids from the C-terminus.
[3]Fragment generated by chymotrypsin digestion of intact esterase consisting of the last C-terminal third of the esterase enzyme.

TABLE 4

Enhancement of the emulsifying activity of apoemulsan in presence of hexadecane using different proteins

| Protein | Maximum emulsifying activity [U/mg. apoemulsan/mg. protein] |
| --- | --- |
| Esterase; RAG-1 | 5580 |
| Esterase; BD4 | 4240 |
| Pancreatic Lipase | 570 |
| Lyzozyme | 720 |
| BSA | 310 |
| Dockerin | 0 |
| Iso-Penicillin Synthetase | 0 |
| Pig Esterase | 0 |

Apoemulsan alone (without protein) gave an emulsification of 700 UpBP under these conditions.

What is claimed is:

1. A bioemulsifier composition useful for forming and stabilizing oil-in-water emulsions, comprising:
   a) an esterase protein of 32.5 kD isolated from cell extracts from at least one strain of Acinetobacter; or recombinant preparations of said esterase protein isolated from esterase-producing vectors expressed in suitable hosts, or peptide fragments of said esterase protein; and
   b) at least one water-soluble polysaccharide polymer.

2. A bioemulsifier composition according to claim 1, wherein the polysaccharide is at least one member selected from the group consisting of agarose, gum arabic, carrageenan, pectin, potato starch, xanthan, dextran, alginic acid, cellulose, chitin, colanic acid, ficoll 400, pullulan, polyvinyl pyrrolydone, stewartan, xylan and *Acinetobacter calcoaceticus* BD4 exopolysaccharide.

3. A bioemulsifier composition according to claim 1, further comprising at least one member selected from the group consisting of a stabilizer and additional emulsifier.

4. A bioemulsifier composition according to claim 1, further comprising at least one member selected from the group consisting of emulsan and apoemulsan.

5. A bioemulsifier composition according to claim 1, further comprising at least one additional low molecular weight surfactant.

6. A bioemulsifier composition according to claim 1, wherein the esterase protein is derived from Acinetobacter strain *A. lwoffi* RAG-1, and has the following amino acid composition:

Met lys phe gly thr val trp lys tyr tyr phe thr glu ser leu leu lys

Ala thr ile arg thr pro ser gln leu asn leu ala pro asn ala leu

Arg pro val leu asp gln leu cys arg leu phe pro gln asn pro

Thr val gln ile arg pro ile arg leu ala gly val arg gly glu glu

Ile lys ala gln ala ser ala thr gln leu ile phe his ile his gly

Gly ala phe phe leu gly ser leu asn thr his arg ala leu met

Thr asp leu ala ser arg thr gln met gln val ile his val asp tyr

Pro leu ala pro glu his pro tyr pro glu ala ile asp ala ile phe asp val

Tyr gln ala leu leu val gln gly ile lys pro lys asp ile ile ile ser gly

Asp ser cys gly ala asn leu ala leu ala leu ser leu arg leu lys gln

Gln pro glu leu met pro ser gly leu ile leu met ser pro tyr leu

Asp leu thr leu thr ser glu ser leu arg phe asn gln lys his asp

Ala leu leu ser ile glu ala leu gln ala gly ile lys his tyr leu thr

Asp asp ile gln pro gly asp pro arg val ser pro leu phe asp asp leu

Asp gly leu pro pro thr leu val gln val gly ser lys glu ile leu leu

Asp asp ser lys arg phe arg glu lys ala glu gln ala asp val lys

Val his phe lys leu tyr thr gly met trp asn asn phe gln met

Phe asn ala trp phe pro glu ala lys gln ala leu ala asp ile ala

Glu phe ala thr ser leu asp leu asp.

7. The composition claimed in claim 1 wherein said esterase protein is produced by at least one technique selected from the group consisting of proteolysis, genetic cloning and chemical synthesis.

8. The composition claimed in claim 1 wherein said water-soluble polysaccharide polymer is derived from at least one source selected from the group consisting of bacterial, plant and biopolymers.

9. The composition claimed in claim 8 wherein said biopolymer comprises at least one polyanionic heteropolysaccharide.

10. A method of forming and stabilizing an oil-in water emulsion comprising adding, to a composition comprising oil and water, a bioemulsifier composition as claimed in claim 1.

11. A method of forming and stabilizing an oil-in water emulsion according to claim 10, additionally comprising the step of adding at least one member selected from the group consisting of a stabilizer and a co-emulsifier to said bioemulsifier composition.

12. A method of forming and stabilizing an oil-in water emulsion according to claim 10, additionally comprising the step of adding at least one member selected from the group consisting of emulsan and apoemulsan to said bioemulsifier composition in an amount necessary to act as a stabilizer or co-emulsifier.

13. A method of forming and stabilizing an oil-in water emulsion according to claim 10, additionally comprising the step of adding at least one low molecular weight surfactant to said bioemulsifier composition.

* * * * *